United States Patent
Byelashov et al.

(10) Patent No.: US 10,190,075 B2
(45) Date of Patent: Jan. 29, 2019

(54) ENRICHMENT OF PALMITOLEIC ACID AND PALMITOLEIC ACID DERIVATIVES BY DRY AND SOLVENT-AIDED WINTERIZATION

(71) Applicant: Omega Protein Corporation, Houston, TX (US)

(72) Inventors: Oleksandr A. Byelashov, Katy, TX (US); Huaixia Yin, Cypress, TX (US); Juan Li, Houston, TX (US); Mark Griffin, Tomball, TX (US)

(73) Assignee: OMEGA PROTEIN CORPORATION, Houston, TX (US)

( * ) Notice: Subject to any disclaimer, the term of this patent is extended or adjusted under 35 U.S.C. 154(b) by 0 days.

(21) Appl. No.: 14/794,673

(22) Filed: Jul. 8, 2015

(65) Prior Publication Data
US 2016/0017257 A1   Jan. 21, 2016

Related U.S. Application Data

(60) Provisional application No. 62/022,120, filed on Jul. 8, 2014.

(51) Int. Cl.
*C11B 7/00* (2006.01)
*A61K 31/201* (2006.01)
*A23D 9/04* (2006.01)

(52) U.S. Cl.
CPC .............. *C11B 7/0025* (2013.01); *A23D 9/04* (2013.01); *A61K 31/201* (2013.01); *C11B 7/0016* (2013.01); *C11B 7/0075* (2013.01)

(58) Field of Classification Search
CPC .............................. C11B 7/0075; C11B 7/0016
See application file for complete search history.

(56) References Cited

U.S. PATENT DOCUMENTS 2,435,626 A * 2/1948 Gooding ............... C11B 7/0083
554/190
2,838,480 A   6/1958 Swern et al.
(Continued)

FOREIGN PATENT DOCUMENTS

GB   1120456 A * 7/1968 ........... B01D 9/0004
JP   1-187089 A   7/1989
(Continued)

OTHER PUBLICATIONS

Aurousseau, B., et al., Compared Fractional Crystallization with urea or from acetone solutions of palmitoleic, heptadecenoic and oleic acids, 1980, Journal of the American Oil Chemists' Society, vol. 53, issue 3, pp. 125-128.*
(Continued)

*Primary Examiner* — Yate K Cutliff
(74) *Attorney, Agent, or Firm* — Morgan Lewis & Bockius LLP

(57) ABSTRACT

The present invention provides a fatty acid mixture enriched with palmitoleic acid and palmitoleic acid derivatives relative to the starting lipid mixture; fractionations procedure describe herein are winterization methods. The invention provides methods of dry winterization and solvent-aided winterization alone and in combination. In some embodiments, the palmitoleic acid and palmitoleic acid derivative enriched mixture described herein contains less than 1% of palmitic acid and palmitic acid derivative. The invention also provides palmitoleic derivatives of use as dietary supplements.

9 Claims, 9 Drawing Sheets

(56) References Cited

U.S. PATENT DOCUMENTS

| | | | | |
|---|---|---|---|---|
| 4,167,519 | A * | 9/1979 | Hock | C11B 7/0041 426/417 |
| 4,228,089 | A * | 10/1980 | Bischof | B01D 9/0004 210/175 |
| 6,461,662 | B2 * | 10/2002 | Cain | A23D 9/00 426/606 |
| 6,492,537 | B2 * | 12/2002 | Foglia | C11B 7/0016 426/417 |
| 2001/0005519 | A1 | 6/2001 | Cain et al. | |
| 2012/0225941 | A1 | 9/2012 | Green | |
| 2013/0129775 | A1 | 5/2013 | Shinde et al. | |

FOREIGN PATENT DOCUMENTS

| | | | | |
|---|---|---|---|---|
| JP | 01-187089 A | | 7/1989 | |
| JP | 2007-070486 | * | 3/2007 | C11C 3/00 |
| WO | WO 2013/086243 A2 | | 6/2013 | |

OTHER PUBLICATIONS

JP 2007-0707486, Kodo Yasumasa et al., Glyceride and Method for Producing the same, 2007, English Translation, 8 pages.*
Matsunaga, T., et al., Screening of Marine cyanobacteria for high palmitoleic acid production, 1995, FEMS Microbiology Letters, vol. 133, pp. 137-141.*
Stoffel, WWilly, et al., Isolation and structure of he C16 unsaturated fatty acids in Menhaden body oil, 1958, Journal of the American Chemical Society, vol. 80, pp. 6604-6608.*
Rusch gen. Klaas, et al., A palmitoleic acid ester concentrate from seabuckthorn pomace, 2004, Eur. J. Lipid Sci. Technol., vol. 106, pp. 412-416.*
Gutierrez, L-F et al., "Palmitoleic Acid Enrichment of Seabuckthorn (Hippophae rhamnoides L.) Pulp Oil by Crystallization Process," Separation Science and Technology, vol. 43, No. 8, Jan. 1, 2008, pp. 2003-2022.

* cited by examiner

R: H, alkyl, heteroalkyl, aryl, heteroaryl, heterocycloalkyl

R: H, alkyl, heteroalkyl, aryl, heteroaryl, heterocycloalkyl

ENRICHMENT OF PALMITOLEIC ACID AND PALMITOLEIC ACID DERIVATIVES BY DRY AND SOLVENT-AIDED WINTERIZATION

CROSS-REFERENCE TO RELATED APPLICATION

This application claims priority to U.S. Provisional Patent Application No. 62/022,120 filed Jul. 8, 2014, the disclosure of which is incorporated herein by reference in its entirety for all purposes.

FIELD OF THE INVENTION

The present invention relates generally to mixtures of fatty acid derivatives that include palmitoleic acid or derivatives, and a process for enriching these mixtures of palmitoleic acid or derivatives by removing one or more contaminating palmitic acid or derivatives from the mixture.

BACKGROUND OF THE INVENTION

Omega-3 fatty acids, also called n-3 poly unsaturated fatty acids ("PUPA"), have long been known to have beneficial effects in humans, particularly with regard to reducing the risk of coronary heart disease, reducing obesity, improving diabetic parameters including blood glucose levels, and improving other parameters relevant to metabolic syndrome. These fatty acids have a number of beneficial effects, among which is lowering elevated blood triglyceride levels down to more clinically acceptable values (Harris et. al., Atherosclerosis (2008); 197(1): 12-24). Omega-3 fatty acids can also assist in weight/fat loss in overweight individuals. Omega-3 fatty acids are typically isolated from marine sources, such as fish oil.

According to the World Health Organization, evidence is "convincing" that consumption of palmitic acid increases the risk of developing cardiovascular diseases, placing it in the same evidence category as trans fatty acids; dietary intake of palmitate and oleate has a broad impact on systemic and tissue lipid profiles in humans." Palmitate raises "bad cholesterol" known as LDL, i.e., low density lipoprotein. Palmitic acid is prepared by treating fats and oils with water at a high pressure and temperature (above 200° C., or 390° F.), leading to the hydrolysis of triglycerides. The resulting mixture is then distilled. Palmitic acid is mainly used to produce soaps, cosmetics, and release agents.

Palmitoleic acid, or(Z)-9-hexadecenoic acid, is an Omega-7 monounsaturated fatty acid that is a common constituent of the glycerides found in human tissue. It is present in all tissues but, in general, found in higher concentrations in the liver. Palmitoleate was shown to possibly influence fatty liver deposition/production, insulin action, palmitate, and fatty acid synthase, leading to the proposal of a new term, "lipokine," having hormone-like effects. As a beneficial fatty acid, it has been shown to increase insulin sensitivity by suppressing inflammation, as well as to inhibit the destruction of insulin-secreting pancreatic beta cells and may have a role in addressing obesity. Palmitoleic acid and derivatives are used in nutritional supplements. Therefore it is of high importance to produce high purity palmitoleic acid and derivatives for such use.

Menhaden oil contains about 30% of Omega-3 fatty acids, which have multiple health benefits. The remaining 70% of oil are non-Omega-3 fatty acids. As the demand for Omega-3 concentrates continues to increase, the manufacturing process generates an increasing quantity of co-products. These co-products are frequently low in Omega-3 fatty acids, but contain other valuable fatty acids, such as palmitoleic acid (POA).

Refined fish oil consists of various fatty acids in triglyceride form, i.e., glycerol backbone with three different fatty acids attached to it. To achieve a meaningful fractionation of fatty acids, triglycerides are often esterified into fatty acid ethyl esters (FAEEs), where each fatty acid is attached to ethanol. Then, FAEEs are passed through a fractional distillation column, which separates the FAEEs by molecular weight. Because of the structural similarity of many fatty acids of nutritional and pharmacological relevance, their purification or the enrichment of a mixture of fatty acids to a desired fatty acid is a challenging process. A convenient and inexpensive method of enriching POA or its derivatives would represent a significant advance in the art. Surprisingly, the present invention provides such a method.

Fats containing palmitoleic acid (C16:1 fatty acid) are known. In fact palmitoleic acid is a component in natural oils such as oils derived from macadamia nuts, which can contain up to 27% of C16:1 fatty acid. Other oils like fish oil or seal blubber contain appreciable amounts of C16:1 fatty acid. Palmitoleic acid is considered to be a healthy oil component, with health benefits such as antitumor activity (JP 59062523, Toyo Jozo Co Ltd), lowering serum cholesterol and LDL (Food Australia 1996, pp 216-222), and protective effects against ventricular arrhythmias as disclosed in U.S. Pat. No. 5,198,250. However, the known fats containing appreciable amounts of C16:1 also contain high amounts of other fatty acids such as C16:0 and C18:1. It would be very beneficial to produce fins that combine high levels of C16:1 with relatively low levels of C16:0. This would improve the performance, such as opacity, purability, viscosity, dosing, and blending of these fats considerably. An attempt to achieve this is disclosed in JP-laid open 01/187 089 (Shikibo Ltd).

One of the known processes to fractionate mixtures of fatty acid is the separation using urea (U.S. Pat. No. 5,078, 920). This method separates relatively saturated species based upon that mixture of straight chain polar organic compounds into fractions respectively richer and poorer of unsaturated material. The more saturated components are complexed with urea to form a clathrate compound.

Another process used for fractionation especially used to increase the ratio of palmitoleic acid compared to palmitic acid is described in U.S. Pat. No. 6,461,662; this process involves a partial enzymatic hydrolysis of material derived from fish oil using an enzyme with specificity for palmitoleic acid and its derivatives, removal of the fatty acid followed by (i) dry fractionation or (ii) wet fractionation. This method is undesirable because it uses of a large amount of solvent.

Because of the structural similarity of many fatty acids of nutritional and pharmacological relevance, their purification or the enrichment of a mixture of fatty acids to a desired fatty acid is a challenging process. What is needed in the art is a convenient, resource- and cost-efficient method to produce oil mixtures that are enriched in palmitoleic acid. Surprisingly, the present invention provides such a method.

BRIEF SUMMARY OF THE INVENTION

In various embodiments, the present invention provides an oil composition that is enriched in palmitoleic acid relative to its palmitic acid concentration. The invention also provides a convenient method for separating palmitic and palmitoleic acids using fractional crystallization.

Fractional distillation of fatty acid esters produces a light fraction and a heavy fraction. The light fraction (Material A) contains high levels of saturated fatty acids (SFAs), mono-unsaturated fatty acids (MUFAs), and very low levels of long-chain polyunsaturated fatty acids (PUFAs). One of the MUFAs in material A is POA (C16:1, Omega-7). Several studies have demonstrated beneficial effects of POA on beta-cell apoptosis induced by glucose or SFA (Morgan N G, Dhayai S: Unsaturated fatty acids as cytoprotective agents in the pancreatic beta-cell. *Prostaglandins Leukot Essent Fatty Acids* 2010, 82:231-236; Morgan N G, Dhayal S, Diakogiannaki E. Welters H J: Unsaturated fatty acids as cytoprotective agents in the pancreatic beta-cell. *Biochem Soc Trans* 2008, 36:905-908), improving circulating lipid profile (Matthan N R, Dillard A, Lecher J L, Ip B, Lichtenstein A H: Effects of dietary palmitoleic acid on plasma lipoprotein profile and aortic cholesterol accumulation are similar to those of other unsaturated fatty acids in the F1B golden Syrian hamster. *J Nutr* 2009, 139:215-221; Griel A E, Cao Y, Bagshaw D D, Cifelli A M, Holub B, Kris-Etherton P M: A macadamia nut-rich diet reduces total and LDL-cholesterol in mildly hypercholesterolemic men and women. *J. Nutr* 2008, 138:761-767. Garg M L, Blake R J, Wills R B: Macadamia nut consumption lowers plasma total and LDL cholesterol levels in hypercholesterolemic men. *J Nutr* 2003, 133:1060-1063.), and improving diabetic conditions by increasing insulin sensitivity (Yang Z, Miyahara H, and Hatanaka A. Chronic administration of palmitoleic acid reduces insulin resistance and hepatic lipid accumulation in KK-Ay mice with genetic type 2 diabetes. *Lipids in Health and Disease*. 2011, 10 (120): 1-8)

Material A contains only about 17% of POA. However, the POA content can be increased by further passing material A through a molecular fractionation system two more times to remove some short-chain and long-chain fatty acids. The POA-enriched fraction (Material B) contains about 29% of POA and a high level of SPA (mainly palmitic acid, PA, 45%). As saturated fatty acids are pro-inflammatory and American Heart Association recommends that their consumption should be limited, a high-POA and low-PA supplement may have a considerable value. However, as POA and PA have similar molecular weights, the separation of POA from PA using fractional distillation is not feasible.

In some embodiments, the present invention provides an oil composition with a POA content of above about 50%. An exemplary composition of the invention is essentially devoid of PA.

In various embodiments, the invention provides an oil composition comprising a mixture of not more than about 0.2% pahnitic acid and at least about 59% palmitoleic acid. In an exemplary embodiment, the oil composition is produced by fractional crystallization of a starting oil mixture containing more than about 0.2% pahrtitlc acid and less than about 59% pahnitoleic acid.

In various embodiments, the composition of the invention is produced by a fractional crystallization producing a liquid olein fraction and a solid stearin fraction. In an exemplary embodiment, the liquid olein fraction comprises not more than about 0.2% palmitic acid and at least about 59% palmitoleic acid. In various embodiments, the oil composition is produced by fractional crystallization of a starting oil mixture containing more than about 0.2% palmitic acid and less than about 59% paimitoleic acid.

In an exemplary embodiment, the composition of the invention is produced by a fractional crystallization comprising, (a) incubating a solution of the starting oil material in an organic solvent at a temperature at which the stearin fraction crystallizes.

In an exemplary embodiment, the composition of the invention is produced by a fractional crystallization comprising, (a) incubating a solution of the starting oil material in an organic solvent at a temperature at which the stearin fraction crystallizes. In various embodiments, the temperature is between about 2° C. and about −50° C.

In various embodiments, the composition of the present invention is produced by a fractional crystallization comprising, (a) incubating a solution of the starting oil material in an organic solvent at a temperature at which the stearin fraction crystallizes, thereby separating the starting oil material into the stearin and the olein fractions; and (b) separating the solid stearin fraction from the liquid olein fraction. In various embodiments, the incubation is for a period of time sufficient for the crystallization to be essentially completed.

In various embodiments, the present invention utilizes an organic solvent. Exemplary organic solvents of use in the invention are selected from an alcohol, a hydrocarbon, a ketone and a mixture thereof.

In various embodiments, prior to step (a), the starting oil material is incubated in the absence of a solvent at a temperature at which the solid stearin fraction crystallizes. The incubation occurs for a time appropriate for the solid stearin fraction to crystallize.

In various embodiments, the fractional crystallization occurs at subambient temperature, e.g., less than about 25° C. Exemplary temperatures for the fractionation or solvent-aided winterization range from about −50° C. to about −6° C. Exemplary temperature ranges for fractionating the oil mixture in the absence of solvent, e.g., the dry winterization can range from about −4 to 2° C.

Other aspects, objects and advantages of the present invention will be apparent from the detailed description that follows.

DETAILED DESCRIPTION OF THE INVENTION

I. Introduction

Figure 1:
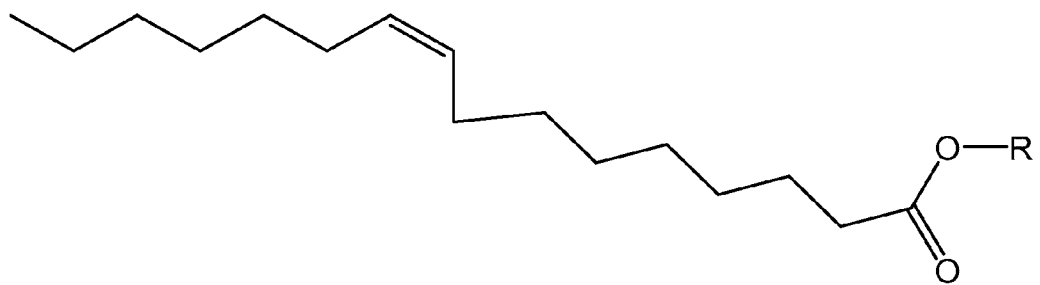
FIG. 1 shows the structure of palmitoleic acid and exemplary derivatives.

Unsaturated fatty acids are vital components of balanced nutrition and have a multitude of uses in food, nutritional supplements and in pharmaceutical formulations. Methods to purify a particular fatty acid or to enrich a mixture of fatty acids in one or more fatty acid are of value in the production of the products in which fatty acids find use such as palmitoleic acid and derivatives. The research indicated that palmitoleic acid could have a role as a signaling molecule affecting body weight, a finding consistent with previous observations that palmitoleic acid, among other fatty acids available in the diet, may be used by enzymes affecting fat oxidation. As a consequence, oil types manufactured with high palmitoleic acid content may have a role in addressing obesity. The present invention provides oil composition enriched with palmitoleic acid and palmitoleic acid derivatives.

II. Abbreviations

PUFA, "polyunsaturated fatty acid"; POA, "palmitoleic acid or C16:1"; POA-R, "palmitoleic acid derivatives"; PA, "palmitic acid or C16:0"; PA-R, "palmitic acid derivatives"; RPM, "revolutions per minute"; DSC, "differential scanning calorimetry"; SFA, "saturated fatty acid"; MLIFA, "monounsaturated fatty acid"; GC, "gas chromatography", FARE, "fatty acid ethyl ester".

III. Definitions

The following terms are used in the claims of the patent as filed and are intended to have their broadest meaning consistent with the requirements of the law. Where alternative meanings are possible, the broadest meaning is intended. All words used in the claims are used in the normal, customary usage of grammar and the English language.

Where substituent groups are specified by their conventional chemical formulae, written from left to right, they optionally equally encompass the chemically identical substituents, which would result from writing the structure from right to left, e.g., —$CH_2O$— is intended to also recite —$OCH_2$—.

Palmitoleic acid derivative (POA-R) refers to an ester, e.g., an alkyl ester, of palmitoleic acid.

Palmitic acid derivative (PA-R) refers to an ester, e.g., an alkyl ester, of palmitic acid.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocycloalkyl groups. An exemplary "R" moiety is the alcohol portion of an ester.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl (e.g., —$CH_2$—$CH_2$—$CH_3$, —$CH_2$—$CH_2$—$CH_2$—), isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl". The term "alkyl" can also mean "alkylene" or "alkyldiyl" as well as alkylidene in those cases where the alkyl group is a divalent radical.

The term "alkylene" or "alkyldiyl" by itself or as part of another substituent means a divalent radical derived from an alkyl group, as exemplified, but not limited, by —$CH_2CH_2CH_2$— (propylene or propane-1,3-diyl), and further includes those groups described below as "heteroalkylene." Typically, an alkyl (or alkylene) group will have from 1 to about 30 carbon atoms, preferably from 1 to about 25 carbon atoms, more preferably from 1 to about 2.0 carbon atoms, even more preferably from 1 to about 15 carbon atoms and most preferably from 1 to about 10 carbon atoms. A "lower alkyl", "lower alkylene" or "lower alkyldiyl" is a shorter chain alkyl, alkylene or alkyldiyl group, generally having about 10 or fewer carbon atoms, about 8 or fewer carbon atoms, about 6 or fewer carbon atoms or about 4 or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, S and B, and wherein the nitrogen and sulfur atoms may optionally be oxidized and the nitrogen heteroatom may optionally be quaternized. The heteroatom(s) O, N, B, S and Si may be placed at any interior position of the heteroalkyl group or at the position at which the alkyl group is attached to the remainder of the molecule. Examples include, but are not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2R'$— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1 (1,2,5,6-tetrahydropyridyl), 2-piperidinyl., 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —OS(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$-U-, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$)alkyl.

As used herein, the term "fused ring system" means at least two rings, wherein each ring has at least 2 atoms in common with another ring. "Fused ring systems may include aromatic as well as nonaromatic rings. Examples of "fused ring systems" are naphthalenes, indoles, quinolines, chromenes and the like.

As used herein, the term "heteroatom" includes oxygen (O), nitrogen (N), sulfur (S), silicon (Si) and boron (B).

"Minimal use" refers to a ratio of solvent to starting oil mixture (w:w) of about 15:1, about 10:1, about 5:1, about 1:1, about 1:2, about 1:3, about 1:4, about 1:5, about 1:6, about 1:7, about 1:8, about 1:9, about 1:10 or about 0:1.

"Starting oil mixture" refers to a mixture of free fatty acids or esters of fatty acids. Exemplary esters include those of palmitic and palmitoleic acids. Exemplary alcohol components of esters include methyl, ethyl, propyl and other $C_1$-$C_6$ alcohols. The starting oil mixture can contain other materials as well, such as fatty acids, salts of fatty acids, glycerol, mono-, di- or tri-glycerides incorporating one or more fatty acid, etc.

"Solvent-aided winterization" refers to fractional separation of a starting oil mixture in the presence of the solvent. An exemplary temperature range is from about −70° C. to about 10° C.

"Dry winterization" refers to fractional separation of oil mixture in the absence of a solvent. An exemplary temperatures range from about −70° C., to about 10° C.

"Pharmaceutically acceptable" means approved by a regulatory agency of the Federal or a state government or listed in the U.S. Pharmacopoeia or other generally recognized. pharmacopoeia for use in animals, and more particularly in humans.

Absolute and relative quantities of fatty acid esters and free fatty acids are set forth herein as wt % or area % of peaks in a chromatogram of a mixture of the invention or a starting oil mixture. In an exemplary embodiment, the chromatogram is produced using the method for fatty acid analysis of the American Oil Chemists Society (AOCS) Ce 1i-07. In an exemplary embodiment, the method utilizes a gas chromatograph (GC): Varian 3900; the column is a SUPELCOWAX-10 fused silica capillary column, 30 m in length, 0.25 mm i.d., 0.25 μm coating of polyethylene glycol (PEG).

"Pharmaceutically acceptable vehicle" refers to a diluent, adjuvant, excipient or carrier with which a compound of the invention is administered. In an exemplary embodiment, a fatty acid or fatty acid mixture prepared by a method of the invention is incorporated into a pharmaceutically acceptable vehicle.

The saponified compounds produced in the methods of the invention contain relatively acidic functionalities; salts of such compounds are included in the scope of the invention. Salts can be obtained by contacting the neutral form of such compounds with a sufficient amount of the desired acid or base, either neat or in a suitable inert solvent. Examples of salts for relatively acidic compounds of the invention include sodium, potassium, calcium, ammonium, organic amino, or magnesium salts, or a similar salts. When compounds of the present invention contain relatively basic functionalities, acid addition salts can be obtained by contacting the neutral form of such compounds with a sufficient amount of the desired acid, either neat or in a suitable inert solvent. Also included are salts of amino acids such as arginate and the like (see, for example, Berge et al., *Journal of Pharmaceutical Science* 1977, 66: 1-19). Certain specific compounds of the present invention contain both basic and acidic functionalities that allow the compounds to be converted into either base or acid addition salts. An exemplary salt is a "pharmaceutically acceptable salt".

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

By "a fatty acid of the Omega-3 group", is meant a polyunsaturated fatty acid, e.g., having at least one double bond. An exemplary location for a double bond is between the carbon atoms at positions 3 and 4 from the end of the hydrocarbon chain. As an example, the fatty acid may include 3, 4, 5 or more double bonds. The fatty acid of the Omega-3 group may include any number of carbon atoms, however, exemplary fatty acids of this group include 18, 20, 22 or 2.4 carbon atoms. For example, the fatty acid of the Omega-3 group may be an α-linolenic acid (ALA; C18:3), a stearidonic acid (SA; C18:4), an eicosatetraenoic acid (ETA; C20:4), an eicosapentaenoic acid (EPA; C20:5), a docosapentaenoic acid (DM; C22:5), or a mixture of at least two of these compounds. The terms "acid", "fatty acid" and "carboxylic acid" optionally encompass esters, e.g., alkyl esters, of these species.

The fatty acids of use in the starting oil mixtures can be derived from essentially any useful source. Exemplary sources are set forth in Table 1.

TABLE 1

Percent by weight of total fatty acids.

| Oil or Fat | Unsat./Sat. ratio | Saturated | | | | | Mono unsaturated | Polyunsaturated | |
| | | Capric Acid C10:0 | Lauric Acid C12:0 | Myristic Acid C14:0 | Palmitic Acid C16:0 | Stearic Acid C18:0 | Oleic Acid C18:1 | Linoleic Acid (ω6) C18:2 | Alpha Linolenic Acid (ω3) C18:3 |
|---|---|---|---|---|---|---|---|---|---|
| Almond Oil | 9.7 | — | — | — | 7 | 2 | 69 | 17 | — |
| Beef Tallow | 0.9 | — | — | 3 | 24 | 19 | 43 | 3 | 1 |
| Butterfat (cow) | 0.5 | 3 | 3 | 11 | 27 | 12 | 29 | 2 | 1 |
| Butterfat (goat) | 0.5 | 7 | 3 | 9 | 25 | 12 | 27 | 3 | 1 |
| Butterfat (human) | 1.0 | 2 | 5 | 8 | 25 | 8 | 35 | 9 | 1 |
| Canola Oil | 15.7 | — | — | — | 4 | 2 | 62 | 22 | 10 |
| Cocoa Butter | 0.6 | — | — | — | 25 | 38 | 32 | 3 | — |
| Cod Liver Oil | 2.9 | — | — | 8 | 17 | — | 22 | 5 | — |
| Coconut Oil | 0.1 | 6 | 47 | 18 | 9 | 3 | 6 | 2 | — |
| Corn Oil (Maize Oil) | 6.7 | — | — | — | 11 | 2 | 28 | 58 | 1 |
| Cottonseed Oil | 2.8 | — | — | 1 | 22 | 3 | 19 | 54 | 1 |
| Flaxseed Oil | 9.0 | — | — | — | 3 | 7 | 21 | 16 | 53 |
| Grape seed Oil | 7.3 | — | — | — | 8 | 4 | 15 | 73 | — |
| Illipe | 0.6 | — | — | — | 17 | 45 | 35 | 1 | — |
| Lard (Pork fat) | 1.2 | — | — | 2 | 26 | 14 | 44 | 10 | — |
| Olive Oil | 4.6 | — | — | — | 13 | 3 | 71 | 10 | 1 |

TABLE 1-continued

Percent by weight of total fatty acids.

| | | Saturated | | | | Mono unsaturated | Polyunsaturated | |
| | | | | | | | | Alpha |
| Oil or Fat | Unsat./Sat. ratio | Capric Acid C10:0 | Lauric Acid C12:0 | Myristic Acid C14:0 | Palmitic Acid C16:0 | Stearic Acid C18:0 | Oleic Acid C18:1 | Linoleic Acid (ω6) C18:2 | Linolenic Acid (ω3) C18:3 |
|---|---|---|---|---|---|---|---|---|---|
| Palm Oil | 1.0 | — | — | 1 | 45 | 4 | 40 | 10 | — |
| Palm Olein | 1.3 | — | — | 1 | 37 | 4 | 46 | 11 | — |
| Palm Kernel Oil | 0.2 | 4 | 48 | 16 | 8 | 3 | 15 | 2 | — |
| Peanut Oil | 4.0 | — | — | — | 11 | 2 | 48 | 32 | — |
| Safflower Oil* | 10.1 | — | — | — | 7 | 2 | 13 | 78 | — |
| Sesame Oil | 6.6 | — | — | — | 9 | 4 | 41 | 45 | — |
| Shea nut | 1.1 | — | 1 | — | 4 | 39 | 44 | 5 | — |
| Soybean Oil | 5.7 | — | — | — | 11 | 4 | 24 | 54 | 7 |
| Sunflower Oil* | 7.3 | — | — | — | 7 | 5 | 19 | 68 | 1 |
| Walnut Oil | 5.3 | — | — | — | 11 | 5 | 28 | 51 | 5 |

*Not high-oleic variety.
Percentages may not add to 100% due to rounding and other constituents not listed.
Where percentages vary, average values are used.

By "a byproduct of an acid of the Omega-3 group", is meant a mixture of saturated, monounsaturated, and polyunsaturated fatty acids and/or fatty acid esters rich in palmitic acid and palmitoleic acid and/or their esters.

A "heavy fraction" defines a fraction rich in long-chain free fatty acids and/or fatty acid esters, including long-chain Omega-3 free fatty acids and/or fatty acid esters thereof.

A "light fraction" defines a fraction rich in short-chain free fatty acids and/or fatty acid esters including palmitic and palmitoleic free fatty acids and/or fatty acid esters thereof.

In the sense of the present invention, by "a food or health diet composition" is meant any type of product intended to be ingested by animals, notably human, which contains a fatty acid or a fatty acid mixture prepared by a method of the invention. Food supplements notably enter the field of protection of the present invention. Food supplements are products to be ingested, as a supplement to current food, in order to compensate for insufficiency of daily intakes of certain compounds. The food or health diet composition of the invention may be in the form of granules, powder, in liquid form naturally or suspended or put into a solution. It may appear in a suitable form for addition to the food ration of an animal or to any other product forming a food supplement. As such, the composition according to the invention may be in a dry, pasty, semi-pasty liquid or semi-liquid form. For example, these may be food products, beverages, food supplements and nutraceutical products.

Among the food products intended for human beings, more particularly relevant to the present invention, mention may be made of oils, margarines and other fats, yoghurts, cheeses, notably fresh cheeses and derived products, fermented products, dairy products, bread, rusks, and other cereal products or derived therefrom (for example pasta), cakes and biscuits, meal substitutes, snacks in general, foods intended for children, babies and infants, creams, desserts, ice creams, chocolate bars, cereal bars, fruit-based compotes.

According to an embodiment and in accordance with the present invention, the composition is in a suitable form for addition to the food ration of an animal. By "animal", is more particularly meant in addition to humans, livestock and notably grazing animals (notably cattle reared for meat, milk and other dairy products, cheese and leather; sheep reared for meat, wool and cheese; goats; pigs), rabbits, poultry (chickens, hens, turkeys, ducks, geese and other poultry) reared for their meats and derived products including eggs, aquatic animals (for example animals from marine farms, fish, shrimps, oysters and mussels), leisure animals and pets (notably horses, dogs, cats, pet birds, aquarium fish), laboratory animals (notably rats and mice).

By "pharmaceutical formulations" is notably but not exclusively meant formulations containing a composition of the invention. The formulation is optionally in solid, liquid, pasty, semi-pasty, or semi-liquid form. When the present invention relates to a pharmaceutical formulation, it optionally contains a pharmaceutically acceptable excipient. The latter is selected so as to be suitable for formulating the composition of the invention. The excipient is adapted to the desired administration route and to the nature of the desired dosage form. The pharmaceutical formulations of the invention include a fatty acid or a mixture of fatty acids of the invention, which is prepared by a method of the invention and they are available in any dosage forms suitable for administration. The dosage forms may notably consist in: tablets, gelatin capsules, powders, granules, lyophilizates, drinkable solutes, syrups, suspensions and suppositories. This list is not exhaustive. The term "tablet" designates any kinds of tablets and notably effervescent tablets, dispersible tablets and orodispersihle tablets.

When the composition of the invention is in the form of a granule or tablet, it may be in a coated form in order to avoid enzymatic destruction which occurs at a certain pH, and at the same time so as to allow controlled release of the active compound in another portion of the digestive tract. The composition according to the invention can also be formulated as sustained release or controlled release tablets.

IV. The Embodiments
IV. Composition

The main constituents of vegetable oils and animal fats are triglycerides, a chemical compound formed from one molecule of glycerol and three fatty acids linked to the central glycerol by ester bonds. Both the physical and the chemical characteristics of oils and fats are greatly influenced by the kind and proportion of the fatty acids on the triacylglycerol. An even number of carbon atoms, from 16 to 18, with a single carboxyl group, is the most common. A number of minor fatty acids may be present in same vegetable sources, including a small amount of branched chain, cyclic and odd number straight chain acids. The ratio of unsaturated to saturated fatty acids in edible oils and fats is very important for human nutrition. Table 1 provides fatty acids composition of some of edible oil mixture.

V. The Embodiments

Figure 2:
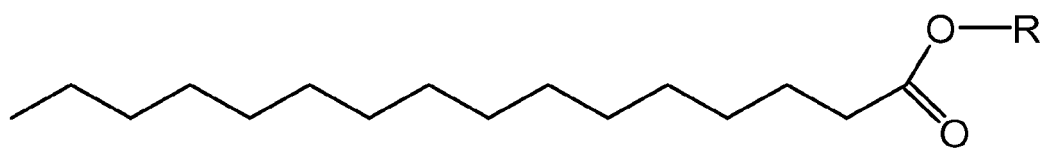
FIG. 2 shows the structure of palmitic acid and exemplary derivatives.

In an exemplary embodiment, the present invention provides an oil composition with a mixture comprises palmitoleic acid (POA) and palmitoleic acid derivatives (e.g., FIG. 1), and palmitic acid (PA) and palmitic acid derivatives (e.g., FIG. 2).

The compositions of the method are prepared by an efficient procedure yielding a composition with a high palmitoleic acid content from a starting oil mixture with a low percent of palmitoleic acid. Exemplary starting oil mixtures comprises at least about 30%, at least about 40%, or at least about 50% palmitic acid. The starting oil mixture comprises less than about 50%, less than about 40%, less than about 30% or less than about 20% palmitoleic acid.

In various embodiments, the present invention provides a starting oil mixture such as oil from macademia nuts, menhaden oil, almond oil, canola oil, cocoa butter, by product of Omega-3 fish oil, cod liver oil, coconut oil, corn oil, cottonseed oil, flaxseed oil, grape seed oil, Illipe, olive oil, palm oil, palm olein, palm kernel oil, peanut oil, sesame oil, shea nut, soybean oil, and walnut oil.

The starting oil mixture can be the product of a fractional distillation prior to fractional crystallization.

In an exemplary embodiment, the present invention provides of producing a composition of the invention using a fractional crystallization that produces a liquid olein fraction comprising not more than 0.2% palmitic acid ester and at least about 59% palmitoleic acid ester.

In various embodiments, the composition of the invention is produced by a fractional crystallization of the starting oil material in an organic solvent at a temperature at which the stearin fraction crystallizes. Exemplary temperatures for the fractionation are between about −20° C. and about −50° C., e.g., from about −35 to about −47° C., In various embodiments, the composition of the invention is prepared by a process for fractional crystallization of an oil mixture. An exemplary process comprises, (a) incubating a solution of the starting oil material in an organic solvent at a temperature at which the stearin fraction crystallizes. In various embodiments, the composition is produced by a method further including, (b) separating the solid stearin fraction from the liquid olein fraction.

The separating can be performed by any convenient means, e.g., filtration, centrifugation, etc. In an exemplary embodiment, the composition of the method is produced by a process that further includes, (c) filtering the liquid olein fraction from the solid stearin fraction.

In various embodiments, the composition of the invention is produced by a process that includes one or more post separation step. For example, in one embodiment, the process further includes, (d) washing the solid olein fraction with an organic solvent. In various embodiments, the solvent is pre-chilled prior to the washing step.

The preceding steps are optionally repeated in any combination any desired number of time depending of the oil mixture.

The process for producing the composition of the invention can be practiced with essentially any organic solvent in which the starting oil mixture is soluble. In various embodiments, the organic solvent for fractioning the starting oil mixture is selected from alcohols, e.g., MeOH, EtOH and i-PrOH; hydrocarbons, e.g., hexanes, petroleum ether; ketones, e.g., acetone, methylethyl ketone; esters, e.g., ethyl acetate; halocarbons, e.g., chloroform, methylene chloride; ethers, e.g., diethyl ether; tetrahydrofuran; aromatics, e.g., toluene; and a mixture thereof.

In some embodiments, the invention provides the step of fractional crystallization of an oil mixture with a minimal use of organic solvent.

In various embodiments, the composition of the method is produced by a solvent-aided fractionation method wherein said organic solvent is EtOH and said starting oil material is dissolved in said solvent in a ratio of starting oil material: EtOH of from about 1.5:1 to about 1:2 (w/w). In various embodiments, the organic solvent is i-PrOH and the starting oil material is dissolved in the solvent in a ratio of starting oil material: i-PrOH of from about 4:1 to about 6:1 (w/w). In various embodiments, the organic solvent is acetone and the starting oil material is dissolved in the solvent in a ratio of starting oil material: acetone of from about 6:1 to about 1:1 (w/w). In an exemplary embodiment, the organic solvent is hexane and the starting oil material is dissolved in the solvent in a ratio of starting oil material:hexane of from about 8:1 to about 12:1 (w/w).

Production of the composition of the invention by separating the fatty acids in the starting oil mixture can be performed using any useful ratio of solvent to starting oil mixture. In an exemplary embodiment, the separation of the fatty acids occurs with minimal use of solvent. Exemplary minimal amounts of organic solvent to starting oil material (w/w) include ratios of about 15:1, about 14:1, about 13:1, about 12:1, about 11:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10 or about 0:1.

In some embodiments, the composition of the invention is produced using fractional solvent-aided winterization of the starting oil mixture with a ratio of (w/w) i-PrOH to fatty acid 1:5, the ratio of WO EtOH to fatty acid 1:1, the ratio of (w/w) EtOH to fatty acid 1.5:1, the ratio of (w/w) hexane to fatty acid 1:10, the ratio of (w/w) acetone to fatty acid 1:2 or acetone to fatty acid 0.5:1.

In various embodiments, the fractional crystallization produces a liquid olein fraction and a solid stearin fraction. An exemplary liquid olein fraction comprises not more than about 0.2% palmitic acid and at least about 59% palmitoleic acid. An exemplary oil composition of the invention is produced by fractional crystallization of a starting oil mixture containing more than about 0.2% palmitic acid and less than about 59% palmitoleic acid.

In various embodiments, the invention provides an oil composition comprising a mixture of not more than about 0.2% palmitic acid and at least about 59% palmitoleic acid. In an exemplary embodiment, the oil composition is produced by fractional crystallization of a starting oil mixture containing more than about 45% palmitic acid and less than about 29% palmitoleic acid.

In various embodiments, the composition of the invention is produced by a fractional crystallization producing a liquid olein fraction and a solid stearin fraction. In an exemplary embodiment, the liquid olein fraction comprises not more than about 0.2% palmitic acid and at least about 59% palmitoleic acid. In various embodiments, the oil composition is produced by fractional crystallization of a starting oil mixture containing more than about 45% palmitic acid and less than about 29% palmitoleic acid.

In some embodiments, the composition of the invention is produced by a method employing a fractional crystallization in the absence of a solvent at a temperature at which the solid stearin fraction crystallizes. The incubation is maintained for a time appropriate for the solid stearin fraction to crystallize. This dry winterization step can be performed either before or after the solvent-aided winterization. In an exemplary embodiment, the dry winterization step is performed before the solvent-aided winterization step. The dry winterization step is optionally performed 1, 2, 3, 4, 5 or more times.

The composition of the invention can be prepared from a starting oil mixture derived from essentially any convenient source. Exemplary sources include a fish oil mixture, oil from macadamia nuts, almond oil, canal oil, cocoa butter, byproduct of Omega-3 fish oil, cod liver oil, coconut oil, corn oil, cottonseed oil, flaxseed oil, grape seed oil, Illipe, olive oil, palm oil, palm olein, palm kernel oil, peanut oil, sesame oil, shea nut, soybean oil, and walnut oil. In an exemplary embodiment of present invention the starting oil mixture includes esters of byproducts of Omega-3 fish oil. Exemplary sources of starting oil mixtures can contain different ratios of POA-R and PA-R such as:

Material A comprising 17% of POA-ethyl ester and 26% of PA-ethyl ester.

Material B comprising 29% of POA-ethyl ester and 45% of PA-ethyl ester.

Fractionation of two byproducts of the production of Omega-3 fish oil ethyl ester concentrates (Material A: POA 17% and PA 26%; Material B: POA 29% and PA 45%) into two fractions of each and production of 3 products: Product A—Fraction 1 from Material A: >20% POA and <12% PA, Product B—Fraction 1 from Material B: >50% POA and <1% PA, and Product C—Fraction 2 from Material B: >80% PA and <4% POA).

In an exemplary embodiment, the starting oil mixture is a product of fractional distillation. which is performed prior to the fractional crystallization.

In some embodiments, the solvent-aided fractionation of the oil mixture produces a. Fraction 1 (Product B) containing less than 1% palatine acid and derivatives, and a Fraction 2 (Product C) rich in pahmtic acid derivatives. An example of a starting oil mixture is a byproduct of Omega-3 fatty acid ethyl ester with a temperature for fractional separation of about −47° C. using solvent such as ethanol.

Fraction 1/Product B: containing more than 50% paimitoleic acid or POA-R and less than 1% palmitic acid or PA-R.

Fraction 2/Product C: containing more than 80% palmitic acid or PA-R and less than 4% palmitoleic acid or POA-R.

Also provided are formulations including a composition of the invention. Exemplary formulations include pharmaceutical, cosmetic, nutraceutical and nutritional formulations.

In various embodiments, the invention provides a method for producing the oil composition of the invention incorporating any of the steps set forth above in any combination.

In various embodiments, the method is a pilot or industrial scale method. In practicing such methods a variety of art-recognized components can be deployed. For example:

1) Crystallization:
  a. Scraped surface crystallizers
  b. Surface-cooled crystallizers)

2) Equipment for separation of olein (liquid) from stearin (solid)
  a. Vacuum drum filter, table filter, horizontal belt filter
  b. Screw press
  c. Glass-lined filter
  d. Membranes filtration
  e. Centrifuge
  f. Screen/scroll centrifuges
  g. Pusher centrifuges
  h. Peeler centrifuges
  i. Decanter centrifuges
  j. Continuous liquid centrifuges
  k. Wash column 3) Equipment for solvent removal
  a. Evaporator:
    i. Natural/forced circulation evaporator
    ii. Falling film evaporator
    iii. Rising film evaporator
    iv. Climbing and falling-film plate evaporator
    v. Multiple-effect evaporator
  b. Wash column The following examples are intended to illustrate various embodiments of the invention. Because they are illustrative, they are not to be interpreted as limiting the scope of the invention in any manner.

VI. Examples

Materials

Fish oil ethyl ester (17.4% POA, 25.9% PA, Material A), ethyl ester (44.97% PA, 28.91% POA, Material B), ethanol (>99.5%), acetone (>99.5%), hexane (>98.5%) and isopropyl alcohol (>99.5%).

EXAMPLE 1

Dry Winterization

Methods

Figure 3:
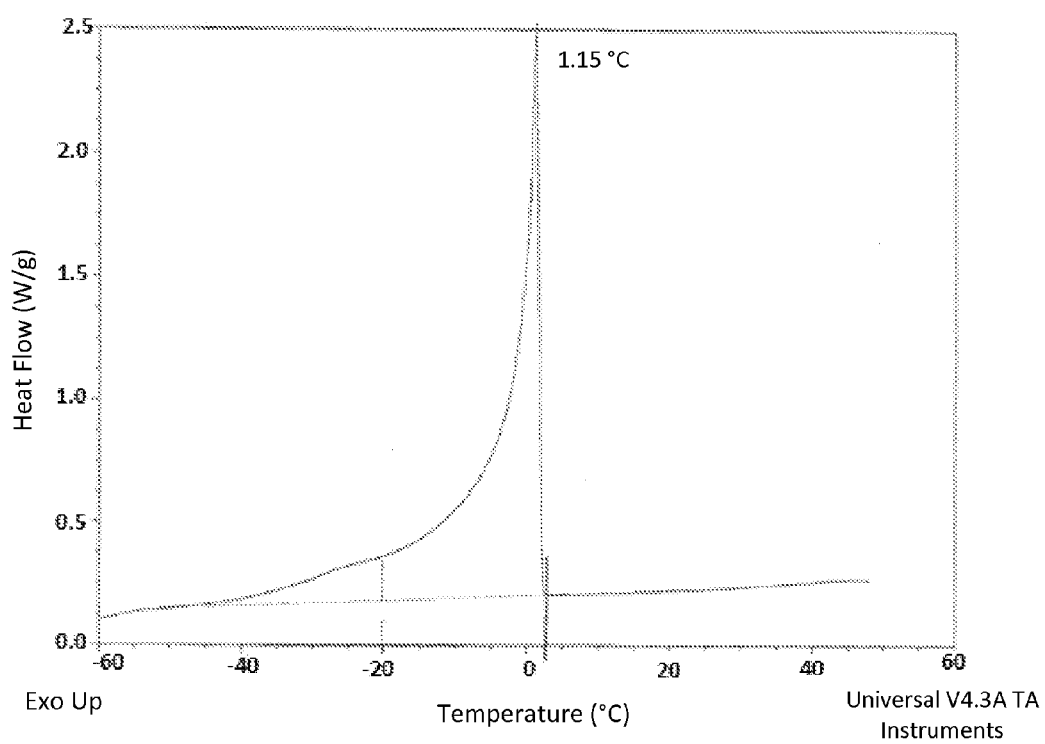
FIG. 3 differential scanning calorimetry of Material A.

Differential scanning calorimetry (DSC) of Material A from 50° C. to −60° C. to estimate the crystallization temperature is illustrated in FIG. 3.

Dry winterization of Material A at different temperatures for different period of time. Material A was stirred at 200 rpm in a jacketed beaker following the conditions below:
1) 1° C. for 180 min
2) 0.5° C. for 120 min
3) −1° C. for 60 min followed by −2° C. for 240 min
4) 2° C. for 30 min followed by 0° C. for 420 min and followed by −4° C. for 12.0 min After winterization, olein (Product A) and stearin were separated by vacuum filtration at corresponding winterization temperatures.

Results and Discussion

1. DSC Scanning Result

The crystallization is an exothermic process. FIG. 3 shows a trend of heat flow with temperature change. The heat flow initiated at 2.5° C., which indicated that Material A started to crystallize at the temperature. At 1.15° C., the heat flow reached the highest point and it means a lot of fatty acids crystallize at the temperature. All the fatty acids were crystallized when temperature goes down to −45° C. The winterization temperatures were selected based on the information.

2. Effect of Temperature on POA Concentration

Fatty acid compositions of Product A that are concentrated by dry winterization at different temperatures are listed in Table 2. Lower temperature favors a higher POA content and lower saturated fatty acids. To concentrate POA to no less than 20% (wt %), the temperature should be at least 0.5° C.

Table describes fatty acid composition of the olein (Product A) concentrated at different temperatures.

TABLE 2

|  | Material A | Product A (1° C.) | Product A (0.5° C.) | Product A (-1~-2° C.) | Product A (2~-4° C.) |
|---|---|---|---|---|---|
| PA (wt %) | 25.9 | 17 | 18 | 12 | 11.8 |
| POA (wt %) | 17.4 | 19.5 | 20.1 | 21.3 | 22.8 |

Note:
Results in Table 2 are shown as wt % of PA and POA.

EXAMPLE 2

Effect of Solvent Wash on Two Step Solvent-Aided Winterization

Methods

Figure 4:
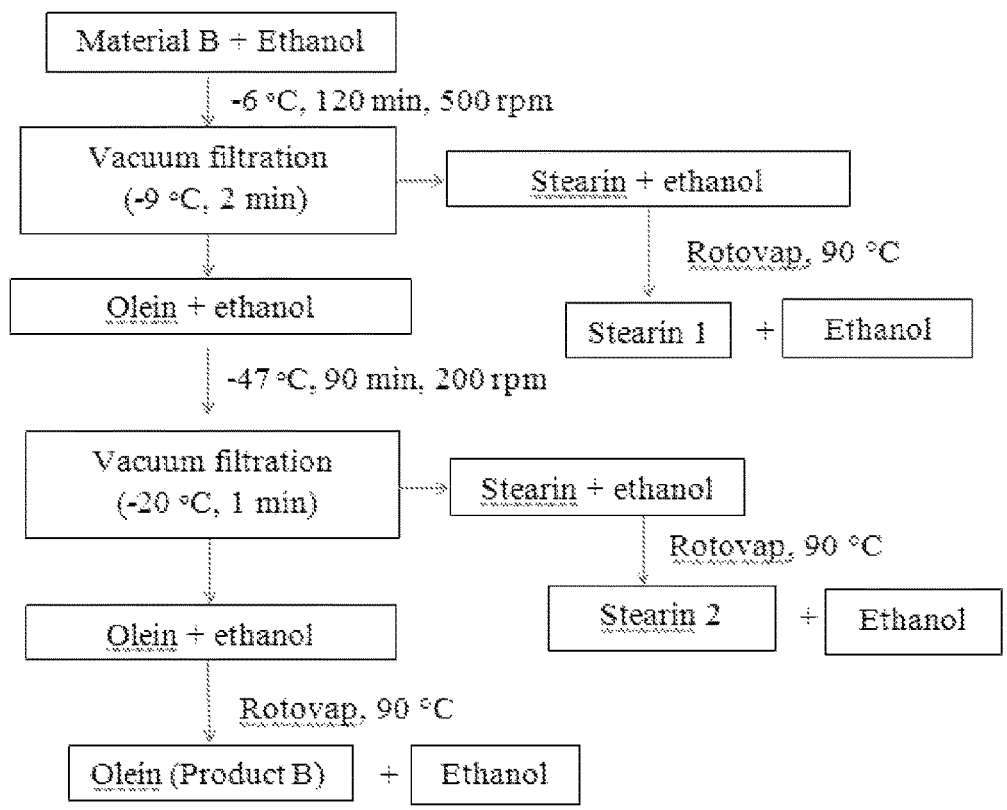
FIG. 4 two-step solvent-aided winterization of Material B without wash of filter cake.

Material B was mixed with ethanol at a ratio of 1:0.75 (w:w, Material B:ethanol) and the mixture was maintained at −6° C. for 120 min with stirring at 500 rpm. Liquid portion was separated from solid portion using vacuum filtration. Filtrate was maintained at −47° C. for another 90 min with stirring at 200 rpm. Then liquid portion was separated from crystals by vacuum filtration. The POA-enriched ethyl ester (olein, Product B) was recovered by removing ethanol from filtrate. The procedure is shown in FIG. 4.

Figure 5:
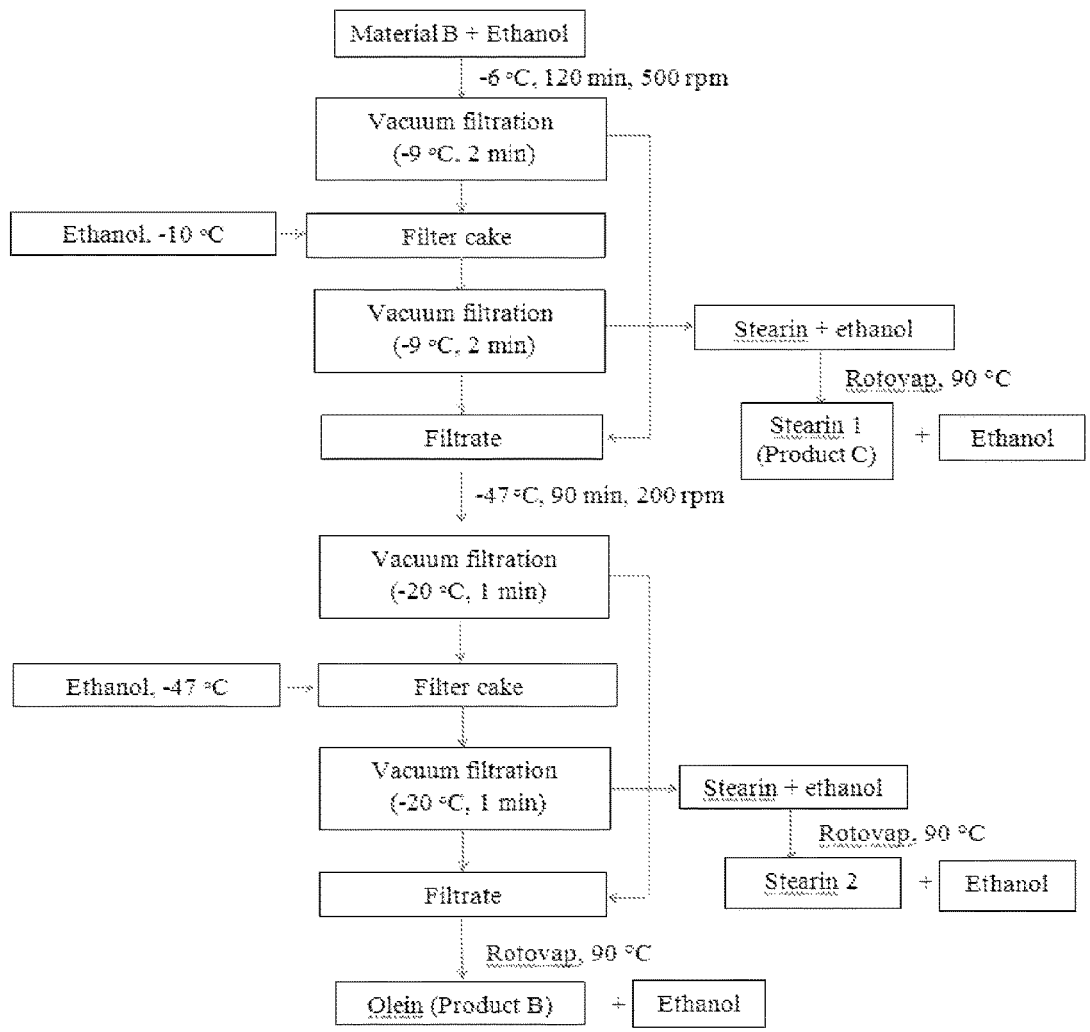
FIG. 5 two-step solvent-aided winterization of Material B with wash of fitter cake.

For comparison, the wash was conducted on both filter cake by pre-chilled ethanol (200 proof) each time, and the washed filtrate was combined with previous filtrate (FIG. 5). Olein was recovered by removing ethanol from filtrate, and stearin was recovered by removing ethanol from filter cake.

Results and Discussion

Washing step increased yield. There was not much difference on PA and POA contents olein that produced with without wash. Due to the increased yield of olein, wash step was desirable and could be applied on all the other winterization procedures.

Table 3 illustrates that PA content in stearin was increased from 79.34% to 91.59% and POA content was decreased from 9.30% to 2.41% with the wash step. PA is a very good emollient and it helps reinforce skin's healthy barrier function for a smoother surface. it has been widely used as the basis for many palmitate ingredients, such as isopropyl palmitate and sodium palmitate. This high PA byproduct (Product C) has a potential to be used as cosmetic ingredients.

TABLE 3

|  | Material B | Without wash | | | With wash | | |
|---|---|---|---|---|---|---|---|
|  |  | Olein | Stearin 1 | Stearin 2 | Olein | Stearin 1 | Stearin 2 |
| PA, % | 44.97 | 0.64 | 79.34 | 29.92 | 0.54 | 91.59 | 56.45 |
| POA, % | 28.91 | 58.45 | 9.30 | 32.68 | 57.57 | 2.41 | 8.45 |

EXAMPLE 3

Effect of Time on Solvent-Aided Winterization for POA

Methods

Figure 6:
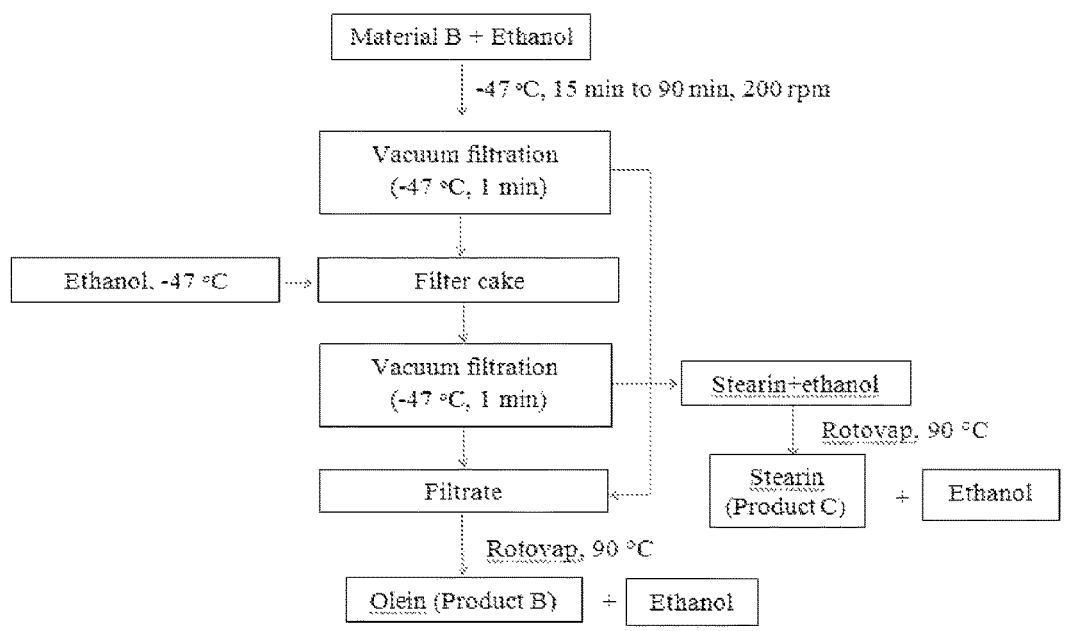
FIG. 6 one-step solvent-aided winterization of Material B with different winterization time.

Material B was mixed with ethanol at ratio of 1:1.4 (w:w, Material B:ethanol) and the mixture was maintained at −47° C. for 15 min to 90 min with stirring at 200 rpm. The liquid portion was separated from the solid portion using vacuum filtration. Filter cake was washed by pre-chilled ethanol (−47° C.) using vacuum filtration, and the washed filtrate was combined with previous filtrate. Olein was recovered by removing ethanol from filtrate, and stearin was recovered by removing ethanol from filter cake (FIG. 6).

Results and Discussion

Different winterization times were tested and the results are presented in Table 4. With different winterization time, PA and POA contents in olein (Product B) were not significantly different, which were about 0.1% and 59%, respectively. PA content in stearin (Product C) was over 80% and POA content was about 4%. There was no effect of winterization time on olein and stearin production. Once the desired temperature was achieved, olein and stearin were separated.

Table 4 illustrates the POA and PA contents in starting material and olein (Product B) and stearin (Product C) fractions after one-step winterization with different time.

TABLE 4

|  |  | 15 min | | 30 min | | 60 min | | 90 min | |
|---|---|---|---|---|---|---|---|---|---|
|  | Material B | Olein | Stearin | Olein | Stearin | Olein | Stearin | Olein | Stearin |
| PA, % | 44.97 | 0.14 | 80.99 | 0.13 | 80.94 | 0.10 | 82.49 | 0.18 | 83.24 |
| POA, % | 28.91 | 59.88 | 3.87 | 59.63 | 4.96 | 59.55 | 3.96 | 59.1 | 3.23 |

EXAMPLE 4

Effect of Temperature on Solvent-Aided Winterization for POA Enrichment

Methods

Figure 7:
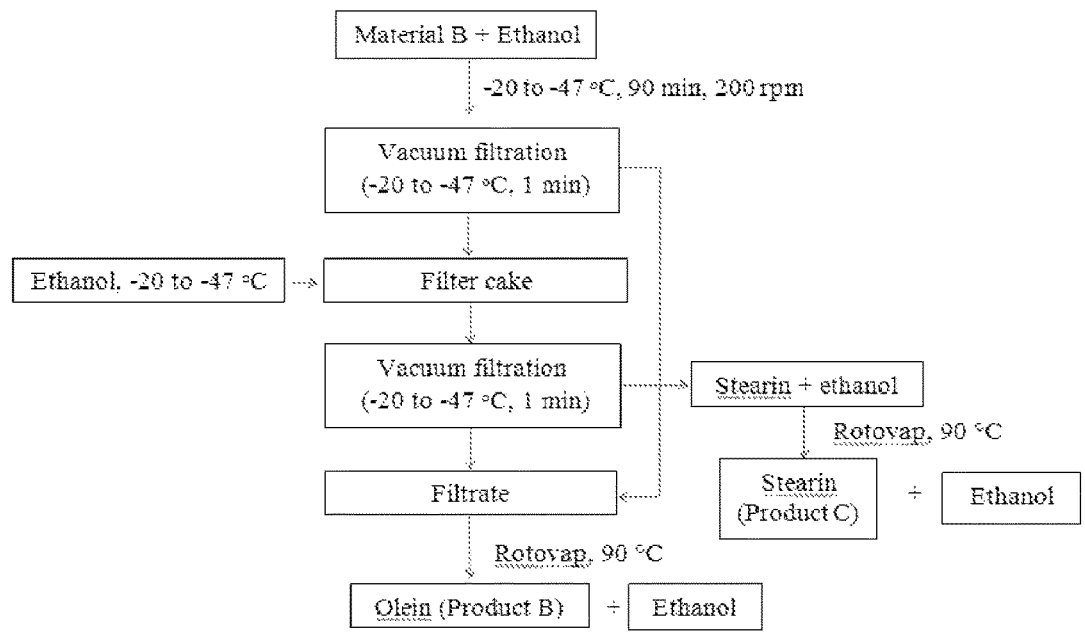
FIG. 7 one-step solvent-aided winterization of Material B at different temperatures.

Material B was mixed with ethanol at ratio of 1:1.4 (w:w, Material B:ethanol) and the mixture was maintained at −20° C. to −47° C. for 90 min with stirring at 200 rpm. Liquid portion was separated from solid portion using vacuum filtration. Filter cake was washed by pre-chilled ethanol using vacuum filtration, and the washed filtrate was combined with previous filtrate. The olein was recovered by removing ethanol from filtrate, and stearin was recovered by removing ethanol from filter cake (FIG. 7).

Results and Discussion

Table 5 demonstrated the role of temperature on POA content of final Product B. With a lower winterization temperature, the POA content was higher, PA content was lower. After winterization at −47° C. POA content was increased from 28.91% to 59.10% and PA content was decreased from 44.97% to 0.18%. The lowest POA content (54.44%) in olein was obtained at −20° C. and the PA content in olein (3.78%) was the highest at the same temperature.

The composition of stearin was dramatically influenced by winterization temperature. By decreasing the temperature from −30° C. to −47° C., most SFAs were crystallized, as well as parts of MUFAs. Thus, the lower the temperature, the higher the POA content in stearin. Stearin (Product C) contained over 80% PA and less than 4% POA with winterization temperature from −30° C. to −47° C.

Based on POA, PA contents of olein and stearin, −40° C. can be selected for POA ethyl ester production.

TABLE 5

| Material B | | −20° C. | | −30° C. | | −35° C. | | −40° C. | | −47° C. | |
|---|---|---|---|---|---|---|---|---|---|---|---|
| | | Olein | Stearin | Olein | Stearin | Olein | Stearin | Olein | Stearin | Olein | Stearin |
| PA, % | 44.97 | 3.78 | 50.01 | 1.04 | 89.39 | 0.98 | 88.89 | 0.48 | 83.75 | 0.18 | 83.24 |
| POA, % | 28.91 | 54.44 | 22.47 | 56.05 | 1.94 | 56.66 | 1.68 | 57.88 | 2.55 | 59.10 | 3.23 |

EXAMPLE 5

Effect of Solvent on Solvent-Aided Winterization for POA Enrichment

Methods

Figure 8:
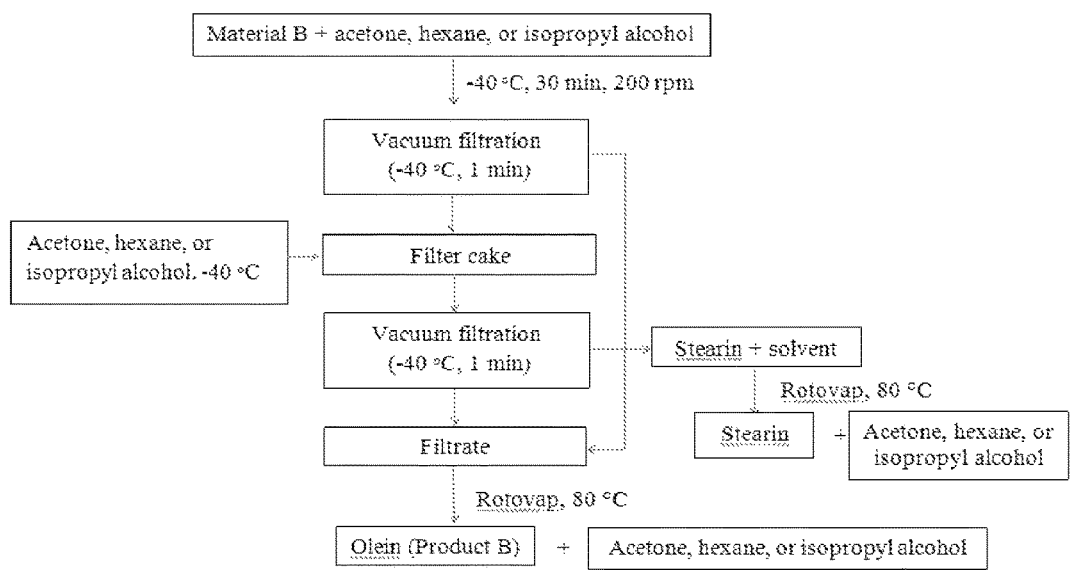
FIG. 8 one-step solvent-aided winterization of Material B with different solvents.

Material B was mixed with solvents acetone, hexane and isopropyl alcohol at ratio of 1:0.147, 1:0.11 and 1:0.187 (w:w, Material B:solvent), respectively and the mixture was maintained at −40° C. for 30 min with stirring at 200 rpm. The liquid portion was separated from the solid portion using vacuum filtration. The filter cake was washed with pre-chilled solvent using vacuum filtration, and the washed filtrate was combined with previous filtrate. The olein was recovered by removing solvent from filtrate, and stearin was recovered by removing solvent from filter cake, FIG. 8.

Results and Discussion

Different solvents such as acetone, hexane and isopropyl alcohol were used for this experiment. The result are summarized in Table 6, PA content was decreased from 39.78% to 0.82% and 0.83% with acetone and isopropyl alcohol, respectively. POA content in Product B was increased to more than 56% with both acetone and isopropyl alcohol. There was no difference on PA and POA contents in olein that produced with acetone and isopropyl alcohol. PA content in olein was 1.57% when winterized with hexane at −40° C. for 30 min. Winterization with ethanol at −40° C. reduced PA content from 44.97% to 0.48%, and increased POA content from 28.91% to 57.88% (Table 5). However, the ratio of ethanol to Material B was much higher than those of acetone and isopropyl alcohol to Material B, which was 1.4:1, 0.15:1 and 0.19:1, respectively. According to USP, ethanol, acetone, and isopropanol are class 3 solvents, while hexane is classified as class 2 solvent which is considered more toxic. Based on fatty acid contents, cost and safety reasons, acetone could be selected for winterization.

Table 6 illustrates POA and PA contents in starting material and olein (product B) and stearin fractions after one-step winterization with different solvent.

TABLE 6

| | Material B | Acetone | | Hexane | | Isopropyl alcohol | |
|---|---|---|---|---|---|---|---|
| | | Olein | Stearin | Olein | Stearin | Olein | Stearin |
| PA, % | 39.78 | 0.82 | 68.63 | 1.57 | 72.78 | 0.83 | 70.94 |
| POA, % | 32.84 | 56.92 | 15.65 | 55.97 | 13.08 | 56.62 | 14.03 |

EXAMPLE 6

Figure 9:
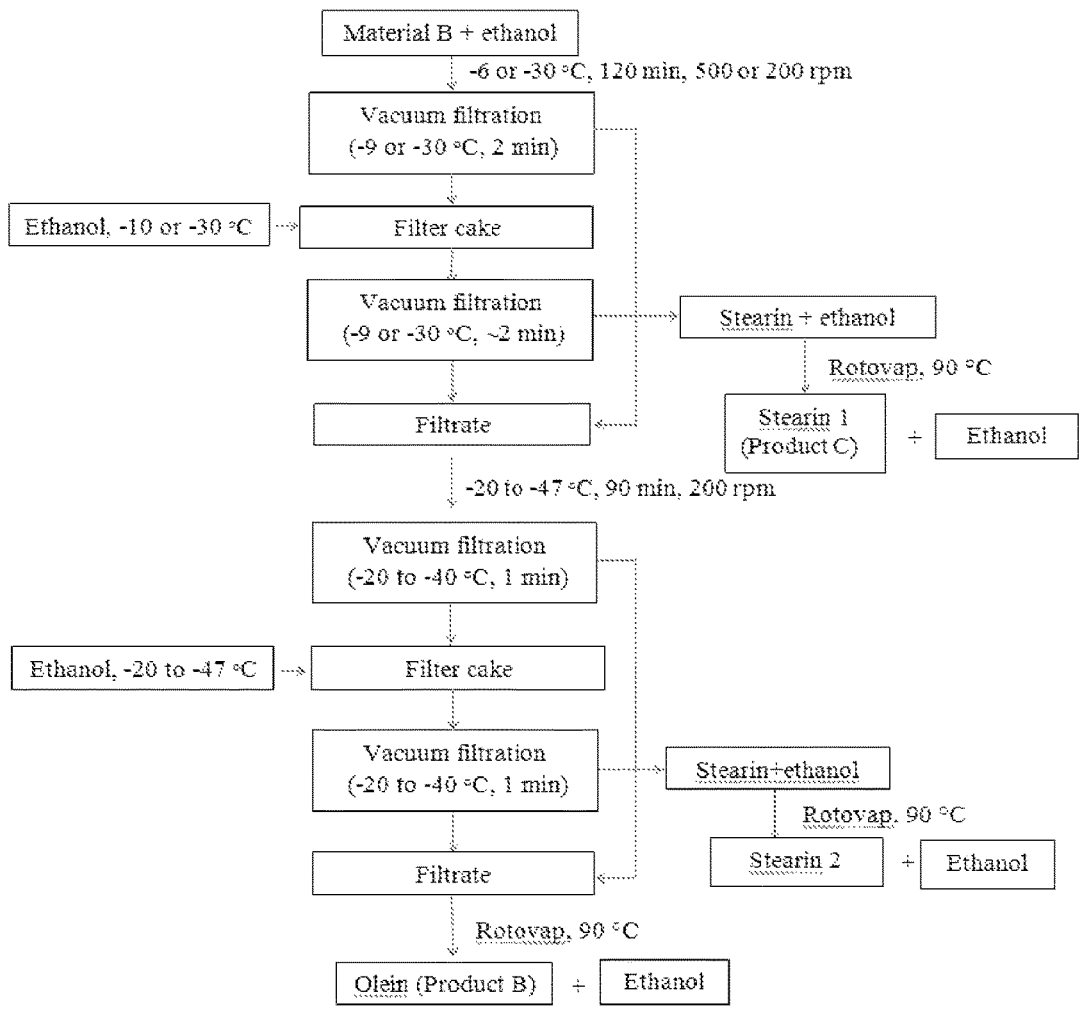
FIG. 9 two-step solvent-aided winterization of Material B at different temperatures.

Effect of Two Step Solvent-Aided Winterization with Different Temperature on POA Enrichment Methods Two step solvent-aided winterization with different temperatures was tested for POA enriched ethyl ester production. Material B was mixed with ethanol at ratio of 1:0.75 (w:w, Material B:ethanol) and the mixture was maintained at 6° C. or −30° C. for 120 min with stirring at 500 rpm. The liquid portion was separated from the solid portion using vacuum filtration. The filter cake was washed by pre-chilled ethanol and the filtrate was combined with the previous filtrate. The filtrate was maintained at 20° C. to −47° C. for another 90 min with stirring at 200 rpm. Then liquid portion was separated from crystals by vacuum filtration. Filter cake was washed by pre-chilled ethanol and the filtrate was combined. Olein was recovered by removing ethanol from filtrate, and stearin was recovered by removing ethanol from filter cake, FIG. 9.

Result and Discussion

In experiments of two step solvent-aided winterization at −6 and −35 to −47° C., PA content was decreased (0.94% to 0.54%), and POA content was increased (56.64% to 57.57%) in olein, respectively (Table 7). PA content in olein was higher than 2% after two-step winterization at −6° C. and −20° C. to −30° C. These results are consistent with the results of one-step winterization experiments (Table 5). After one-step winterization at −35° C., PA and POA contents were 0.98% and 56.66% in olein, respectively. These results were very close to 0.94% (PA) and 56.64% (POA) in olein after two-step winterization at −6° C. and −35° C. Also after the first time winterization in two-step winterization process, stearin (Product C) had a high PA (>85%) and low POA (<4%) contents (Table 7). Overall, one-step winterization is more efficient than two-step winterization process.

Table 7 describes the POA and PA contents in starting material and olein (Product B) and stearin fractions (Product C) after two-step winterization with different temperature.

TABLE 7

| | Material B | −6 and −20° C. | | −6 and −30° C. | −6 and −35° C. | | −30 and −40° C. | | | −6 and −47° C. | | |
|---|---|---|---|---|---|---|---|---|---|---|---|---|
| | | Olein | Stearin 2 | Olein | Olein | Stearin 2 | Olein | Stearin 1 | Stearin 2 | Olein | Stearin 1 | Stearin 2 |
| PA, % | 44.97 | 3.78 | 50.01 | 2.2 | 0.94 | 71.58 | 0.73 | 89.39 | 17.09 | 0.54 | 91.16 | 56.46 |
| POA, % | 28.91 | 54.44 | 22.47 | 50.5 | 56.64 | 0.36 | 57.36 | 1.94 | 7.13 | 57.57 | 2.41 | 8.45 |

EXAMPLE 7

Determining Content of Palmitoleic and Palmitic Acid

Fatty acid profiles of Material A, Material B, Product A, Product B and Product C were determined by gas chromatography (GC, Varian 3900). AOCS (American Oil Chemists' Society) official method Ce 2-66 was used to methylate ethyl esters. SUPELCOWAX-10 fused silica capillary column was used. It's 30 m in length, 0.25 mm i.d. with 0.25 μm coating of polyethylene glycol (PEG). GC operating conditions were the same as the AOCS official method Ce 1i-07. Helium was used as carrier gas.

The Examples set forth herein provide exemplary procedures to separate two major components of Omega-3 fish oil byproducts using dry and solvent aided winterization to enrich the palmitoleic ethyl ester. In the dry winterization process, Product A (POA>20% and PA<12%) was produced at temperature below about 0.5° C. In solvent-aided winterization process, a one-step winterization process had a similar effect as two-step winterization on POA enrichment, and a wash step increased olein yield. Winterization time had no effect on POA enrichment, while temperature played an important role in POA enrichment. (Mein that produced at −40° C. contained 0.48% PA and 57.88% POA. Winterization with acetone had lower solvent to Material B ratio (0.15:1) than ethanol (1.4:1) and isopropyl alcohol (0.19:1), and PA was reduced to below 1% and POA was increased to over 50%. One-step solvent-aided winterization at −40° C. with acetone could be used to concentrate POA (Product B). Due to the high POA (>50%) and low PA (<1%) contents, Product B can be used as food supplement. Stearin (Product C) that produced during solvent-aided winterization contains high saturated fat with high PA (>80%) and low POA (<4%) contents, it can be used in cosmetics.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

All publications, patents, and patent applications cited herein are hereby incorporated by reference in their entirety for all purposes.

What is claimed is:

1. A method for producing an oil composition of a liquid olein fraction that is not derived from algae, wherein the oil composition comprises a mixture of not more than 0.2% (wt %) palmitic acid and at least 59% (wt %) palmitoleic acid from said liquid olein fraction, said method comprising fractional crystallization of a starting oil mixture containing more than 0.2% (wt %) palmitic acid and less than 59% (wt %) palmitoleic acid to produce the liquid olein fraction and a solid stearin fraction, and wherein said fractional crystallization comprises:
   (a) incubating a solution of said starting oil mixture in an organic solvent at a ratio of organic solvent to starting oil mixture at a temperature between about −20° C. to about −70° C. to produce said solid stearin fraction and said liquid olein fraction, wherein said organic solvent is selected from methanol, ethanol, isopropyl alcohol, acetone, and hexane, and wherein the ratio of methanol to the starting oil mixture is 2:1 to 1:1, the ratio of ethanol to the starting oil mixture is 2:1 to 1:1, the ratio of isopropyl alcohol to the starting oil mixture is 1:4 to 1:6, and the ratio of acetone to the starting oil mixture is 1:6 to 1:8, or the ratio of hexane to the starting oil mixture is 1:8 to 1:10;
   (b) separating said solid stearin fraction and said liquid olein fraction; and
   (c) collecting said liquid olein fraction to produce the oil composition of said liquid olein fraction.

2. The method according to claim 1, wherein said starting oil mixture comprises at least 30% (wt %) palmitic acid.

3. The method according to claim 1, wherein said starting oil mixture comprises less than 50% (wt %) palmitoleic acid.

4. The method according to claim 1, wherein separating at step (b) comprises filtering said liquid olein fraction from said solid stearin fraction.

5. The method according to claim 1, further comprising washing said solid stearin fraction with the organic solvent of step (a) after step (b).

6. The method according to claim 1, wherein said temperature ranges from −35° C. to −47° C. to produce the crystallized solid stearin fraction and the liquid olein fraction.

7. The method of according to claim 1, wherein the starting oil mixture is a fish oil mixture, oil from macadamia nuts, almond oil, canola oil, cocoa butter, by product of omega-3 fish oil, cod liver oil, coconut oil, corn oil, cottonseed oil, flaxseed oil, grape seed oil, olive oil, palm oil, palm olein, palm kernel oil, peanut oil, sesame oil, shea nut, soybean oil, and walnut oil.

8. The method of according to claim 1, wherein the starting oil mixture is Menhaden oil.

9. The method of according to claim 1, wherein said starting oil mixture is a product of fractional distillation.

* * * * *